(12) United States Patent
Saur et al.

(10) Patent No.: US 12,727,961 B2
(45) Date of Patent: Sep. 8, 2026

(54) METHOD FOR OPERATING A MICROSURGICAL VISUALIZATION SYSTEM, AND MICROSURGICAL VISUALIZATION SYSTEM

(71) Applicant: CARL ZEISS MEDITEC AG, Jena (DE)

(72) Inventors: Stefan Saur, Oberkochen (DE); Johannes Rangel, Oberkochen (DE)

(73) Assignee: CARL ZEISS MEDITEC AG, Jena (DE)

( * ) Notice: Subject to any disclaimer, the term of this patent is extended or adjusted under 35 U.S.C. 154(b) by 340 days.

(21) Appl. No.: 18/525,836

(22) Filed: Nov. 30, 2023

(65) Prior Publication Data

US 2024/0189064 A1 Jun. 13, 2024

(30) Foreign Application Priority Data

Dec. 9, 2022 (DE) ..................... 10 2022 213 395.1

(51) Int. Cl.
*H05B 47/125* (2020.01)
*A61B 90/00* (2016.01)
(Continued)

(52) U.S. Cl.
CPC ............ *A61B 90/361* (2016.02); *A61B 90/30* (2016.02); *H05B 47/125* (2020.01); *G06V 40/193* (2022.01)

(58) Field of Classification Search
CPC .................................................... H05B 47/125
See application file for complete search history.

(56) References Cited

U.S. PATENT DOCUMENTS 7,505,201 B2 3/2009 Oelckers et al.
7,933,066 B2 4/2011 Steffen et al.
(Continued)

FOREIGN PATENT DOCUMENTS

DE 102005011121 A1 5/2006
DE 202006020039 U1 9/2007
(Continued)

OTHER PUBLICATIONS

Van Norren et al., "Light Damage to the Retina: an Historical Approach", Cambridge Ophthalmological Symposium, Eye, 2016, vol. 30, pp. 169-172.

*Primary Examiner* — Young Lee
(74) *Attorney, Agent, or Firm* — NIXON PEABODY LLP; Jeffrey L. Costellia

(57) ABSTRACT

The invention relates to a method for operating a microsurgical visualization system, wherein the microsurgical visualization system comprises at least one camera for capturing a capture region and at least one illumination source for illuminating at least a part of the capture region, wherein a presence of an eye area of a patient in an image captured by means of the at least one camera is identified, wherein a region in the captured image illuminated by the at least one illumination source is identified and/or the illuminated region is determined, and wherein an irradiance is reduced, at least in the identified eye area, by controlling the at least one illumination source if an overlap between the eye area and the illuminated region is ascertained. The invention also relates to a microsurgical visualization system.

12 Claims, 4 Drawing Sheets

(51) Int. Cl.
*A61B 90/30* (2016.01)
*G06V 40/18* (2022.01)

(56) References Cited

U.S. PATENT DOCUMENTS

| | | | | |
|---|---|---|---|---|
| 8,154,797 | B2 | 4/2012 | Steffen et al. | |
| 8,520,303 | B2 | 8/2013 | Steffen et al. | |
| 9,717,401 | B1 * | 8/2017 | Orringer | A61B 1/0692 |
| 2006/0087729 | A1 | 4/2006 | Oelckers et al. | |
| 2008/0049314 | A1 | 2/2008 | Steffen et al. | |
| 2010/0302629 | A1 | 12/2010 | Steffen et al. | |
| 2011/0164315 | A1 | 7/2011 | Steffen et al. | |
| 2018/0310384 | A1 * | 10/2018 | Chang | A61B 90/35 |
| 2020/0214787 | A1 * | 7/2020 | Hallack | H04N 23/61 |
| 2021/0325649 | A1 | 10/2021 | Segev et al. | |

FOREIGN PATENT DOCUMENTS

| | | | |
|---|---|---|---|
| DE | 102006047723 | A1 | 2/2008 |
| DE | 102007054686 | A1 | 5/2009 |
| DE | 102022100626 | A1 | 7/2023 |
| JP | 200117459 | A | 1/2001 |

* cited by examiner

METHOD FOR OPERATING A MICROSURGICAL VISUALIZATION SYSTEM, AND MICROSURGICAL VISUALIZATION SYSTEM

CROSS-REFERENCE TO RELATED APPLICATIONS

The present application claims priority under 35 U.S.C. § 119 to German Patent Application No. 10 2022 213 395.1, filed Dec. 9, 2022, the contents of which are incorporated by reference herein in their entirety.

The invention relates to a method for operating a microsurgical visualization system, and to a microsurgical visualization system.

In the field of microsurgery, especially within the scope of operations on the brain, digital stereoscopic surgical microscopes are opening up new workflows for acquiring and preparing information from the visualized surgical scene. For example, three-dimensional information about the head of the patient is obtained from captured microscope images within the scope of a topography-based patient registration for brain surgery, in order to bring three-dimensional information of the patient acquired preoperatively (e.g., computed tomography or MRI data) into correspondence with a determined reference frame of the patient. To this end, a plurality of strongly illuminated images of the head of the patient are captured from different perspectives. In so doing, there is a need for compromise between a brightness of the light source of the microscope and a signal-to-noise ratio of the images in order to reduce, or preferably entirely avoid, the risks of phototoxicity or thermal damage for the irradiated tissue of the patient, but at the same time obtain great accuracy of the calculated topography data.

To date, phototoxic effects of the light source in the microscope on brain tissue of a patient are prevented with the aid of limit values from predefined brightness values considered safe, below which the brightness of the light source can be controlled either manually or automatically. These upper limit values are established on the basis of optical properties of the microscope, with for example light filters, a focal length, magnification settings, properties of the light source, and guidelines for photo safety being taken into account.

The light sources of surgical microscopes used in neurosurgery (brain and spinal column) are optimized such that they offer a sufficient illumination even in deep channels. Thus—in contrast to specific surgical microscopes for eye surgery—they are not suitable for the illumination of eye tissue, especially if the eyes of the patient are open.

A further problem is that the eyes of a patient under anesthesia no longer have an optical reflex. Moreover, the eyes in general do not have an optical reflex for light in the infrared wavelength range, with the result that the eyes are not automatically closed if too strong infrared light is incident on the retina, even outside of anesthesia.

DE 10 2006 047 723 A1 has disclosed a surgical microscope suitable for use in neurosurgery in particular. The surgical microscope has an illumination device for the provision of illumination light in an operating region examined by the surgical microscope. The illumination device contains a high-power light source comprising intensity setting means. The intensity setting means allow the intensity of the illumination light guided to the object region to be set between a maximum value and a minimum value. The surgical microscope has a control unit for the illumination device, said control unit comprising an operating module by means of which the illumination device can be activated and controlled. To set the intensity of the illumination light guided to the operating region, the control unit is operatively connected to the settable filter unit. Provision is made for a signal generator which emits a warning signal if an intensity of illumination light which exceeds a safety limit value stored in a memory is set by means of the operating module.

JP 2001 017 459 A has disclosed a surgical microscope. The microscope comprises an optical illumination system for radiating illumination light from a light source on an object eye, and an optical observation system for observing the object eye. It also comprises a photoelectric transducer element for detecting reflection light from the observed eye, an instantaneous value operating device for providing an instantaneous value of the luminous illumination energy of the illumination light toward the observed eye on the basis of a detection signal from the photoelectric transducer element, an instantaneous luminous energy value table for storing tolerable instantaneous value data of the illumination light toward the observed eye, and a luminous energy setting device for comparing the result of the provision by the instantaneous value actuation device with the tolerable instantaneous value data stored in the instantaneous luminous energy value table and for setting the luminous illumination energy of the illumination light for the observed eye by setting the luminous illumination energy emanating from the light source, in correspondence with the difference between the luminous illumination energy of the illumination light for the observed eye and the tolerable instantaneous value data.

D. van Norren and J. J. Vos, *Light Damage to the retina: an historical approach*, Eye 30, pp. 169-172, 2016, Macmillan Publishers Limited, provides a historic overview of the development of research regarding the damage to the retina by light.

The invention is based on the object of developing a method for operating a microsurgical visualization system and a microsurgical visualization system, by means of which an eye area can be better protected against irradiance that is too high, especially while carrying out an illumination-intensive patient registration.

According to the invention, the object is achieved by a method having the features of patent claim 1 and a microsurgical visualization system having the features of patent claim 10. Advantageous configurations of the invention are evident from the dependent claims.

One of the basic ideas of the invention is that of identifying a presence of an eye area of a patient in an image captured by means of at least one camera of the microsurgical visualization system. Further, a region in the captured image illuminated by at least one illumination source of the microsurgical visualization system is identified and/or the illuminated region is determined, for example calculated. To protect the eyes of the patient, an irradiance is reduced, at least in the identified eye area, by controlling the at least one illumination source if an overlap between the identified eye area and the identified and/or determined illuminated region is ascertained. Thus the irradiance of the illumination source is reduced if the illuminated region at least partially coincides with the identified eye area. This can effectively protect the eyes of the patient from phototoxic damage.

In particular, a method for operating a microsurgical visualization system is provided, wherein the medical visualization system comprises at least one camera for capturing a capture region and at least one illumination source for illuminating at least a part of the capture region, wherein a presence of an eye area of a patient in an image captured by means of the at least one camera is identified, wherein a region in the captured image illuminated by the at least one illumination source is identified and/or the illuminated region is determined, and wherein an irradiance is reduced, at least in the identified eye area, by controlling the at least one illumination source if an overlap between the eye area and the illuminated region is ascertained.

Further, a microsurgical visualization system in particular is developed, comprising: at least one camera configured to capture a capture region; at least one illumination source configured to illuminate at least a part of the capture region; and a control device, wherein the control device is configured to identify a presence of an eye area of a patient in an image captured by means of the at least one camera, to identify a region in the captured image illuminated by the at least one illumination source, and/or to determine the illuminated region, and to reduce an irradiance, at least in the identified eye area, by controlling the at least one illumination source if an overlap between the eye area and the illuminated region is ascertained.

An advantage of the method and microsurgical visualization system is that no further devices, such as for example an additional photosensor, are required to effectively protect the eyes of the patient. An effective protection for the eyes can be provided in this way, especially in the field of brain surgery where the eyes themselves are not part of the operation.

A microsurgical visualization system is, in particular, a microsurgical surgical microscope, in particular a stereoscopic microsurgical surgical microscope. A microsurgical visualization system exhibits a light-based operation in particular, which is to say a capture region is illuminated by means of light in particular and a specularly and/or diffusely reflected light is captured by means of the at least one camera, in particular by virtue of the light being guided to the camera via an imaging optical unit. The microsurgical visualization system is especially configured for at least one of the following fields of application: neurosurgery; dental surgery; ears, nose, and throat (ENT) surgery; plastic surgery; and reconstructive surgery. In particular, a field of application of the microsurgical visualization system is outside of ophthalmology.

For example, the at least one camera can be a camera which captures light via a beam path, especially via an imaging optical unit, of the microsurgical visualization system. In principle, the at least one camera can also be a (stereo) camera of a stereoscopic microsurgical visualization system.

However, the at least one camera can also be a surround camera of the microsurgical visualization system, which is configured to capture the capture region and, in particular, a surround of the capture region independently of a beam path and an imaging optical unit of the microsurgical visualization system. For example, such a surround camera serves to navigate and/or track surgical instruments and/or optical markers. In particular, this may be implemented in the near infrared or infrared wavelength range, with the result that the surround camera can be configured to capture light in the near infrared or infrared. In this case, the surround camera may be integrated in a housing of the microsurgical visualization system, or else be arranged on the outside of such a housing.

If a plurality of cameras are provided, then the method can be carried out for each camera, with the reduction being performed if an overlap is ascertained using a captured image from at least one of the cameras as a starting point.

Provision can be made for a gain and a shutter speed to be considered during the identification of the eye area and, in particular, the illuminated region. This is particularly advantageous if an autogain function is realized.

An irradiance is defined, in particular, as a radiant flux, which is to say a power, through a receiver surface. In this case, the associated physical unit is $W/m^2$ in particular, which is to say watts per square meter.

The at least one illumination source can be an illumination source in the visible wavelength range. However, the at least one illumination source could also be an illumination source in the near infrared and/or infrared wavelength range and, in particular, only emit light from outside of the visible wavelength range.

If a plurality of illumination sources are provided, then the method is carried out for each of the illumination sources in particular, with the reduction being performed if an overlap with an illuminated region from at least one of the illumination sources is ascertained.

Identifying the eye area in the captured image can be implemented in particular by means of pattern recognition methods, computer vision methods, and/or artificial intelligence methods, which are known per se. By way of example, characteristic features and/or patterns (e.g., a pupil) can be identified for eyes. To this end, use can be made, for example within the scope of image processing, of suitable filters and/or a trained machine learning method, for example a deep neural network trained for the identification of eyes, in particular a convolutional neural network, as have already been used for several years now in photographic cameras and cameras of smartphones (e.g., by way of object and/or feature recognition, semantic segmentation, etc.). In particular, the machine learning method is trained with the aid of marked and/or annotated images. Further, use can also be made of, for example, a pattern recognition method according to the Viola-Jones framework.

In particular, the identified eye area is defined in the captured image as a set of picture elements which, for example, can also be described as a set of picture element coordinates.

Identifying the illuminated region can be implemented in particular by means of pattern recognition methods, computer vision methods, and/or artificial intelligence methods, which are known per se. For example, characteristic features and/or patterns can be identified in the captured image (e.g., patterns in a brightness profile, etc.). For example, a trained machine learning method, for example a trained deep neural network, in particular a convolutional neural network, can also identify, in particular estimate, the illuminated region in the captured image. In particular, the machine learning method is trained with the aid of marked and/or annotated images.

In particular, the illuminated region is determined using known properties of the illumination source as a starting point, for example an illumination origin, geometric imaging and/or propagation properties of a light field (i.e., a "light cone" in particular) emanating from the illumination origin, and a spectral distribution. From this, a light spot generated by the light field and forming the illuminated region can be determined in distance-dependent fashion. In particular, there can be a (computational or virtual) projection onto a surface, for example a face of a patient, in the process. In particular, an irradiance can be calculated for each three-dimensional position. In the process, use can also be made of models which can be parameterized with the aid of empirical test series.

In particular, the illuminated region is identified and/or determined within the captured image as a picture element set, described for example as a set of associated picture element coordinates.

In a simple case, the illuminated region is approximated as a binary intensity curve independently of a specific value of the irradiance at individual positions (in particular picture element coordinates) within the illuminated region, in the case of which an irradiance of zero is assumed outside of the illuminated region and an irradiance with an estimated positive, more particularly constant, value is assumed within the illuminated region.

In particular, the identified and/or determined illuminated region is defined in the captured image as a set of picture elements which, for example, can be described as a set of picture element coordinates.

An exemplary application scenario for the method and microsurgical visualization system for example comprises a patient registration which is carried out prior to an operation and within the scope of which optical markers arranged on the patient are captured by means of the at least one camera in order to locate a topography of the patient in a three-dimensional reference coordinate system. As a rule, a plurality of stereoscopic images are captured from different directions during the patient registration. A movement required to this end can be implemented by means of a robotic stand of the microsurgical visualization system in automated fashion or by a manual movement of the microsurgical visualization system. The patient registration requires high levels of irradiance. On account of the need to capture the head of the patient from different directions, the light field from the illumination source can potentially overlap with the eye area. The eyes of the patient, who is already anesthetized during the registration, can be effectively protected by means of the method and microsurgical visualization system: If an overlap between the identified eye area and the illuminated region is identified, then the irradiance is reduced, at least in the identified eye area, by controlling the at least one illumination source.

Parts of the microsurgical visualization system, in particular the control device, can be designed, either individually or together, as a combination of hardware and software, for example as program code that is executed on a microcontroller or microprocessor.

However, provision can also be made for parts to be designed as application-specific integrated circuits (ASICs) and/or field-programmable gate arrays (FPGAs), either on their own or in combination.

An embodiment provides for an eyelid status to be identified in the captured image, the reduction in the irradiance being performed taking account of the identified eyelid status. In particular, an eyelid status comprises at least the two states of "open" and "closed". Identifying and taking account of the eyelid status of the patient allows a more finely set reduction to be implemented, the latter being matched to the eyelid status and hence to the extant risk to the retina of the eyes of the patient. Further, it is possible to prevent an unnecessary reduction in the irradiance, with the result that a functionality of the illumination, especially during an illumination-intensive patient registration, is only restricted if this is required in order to protect the retina. Since the risk of damage is significantly reduced in the case of a closed eye as the eyelid generally already offers protection, it is thus possible to flexibly react to the specific situation present. In particular, a reduction in that case need only be implemented to the extent necessary to protect the eyes of the patient. For example, an irradiance in the case of an open eyelid can be reduced to a greater extent than in the case of a closed eyelid. Identifying the eyelid status in the captured image can be implemented in particular by means of computer vision methods, and/or artificial intelligence methods, which are known per se. For example, characteristic features for the eye (e.g., a pupil) can be identified in the open state or in the closed state. To this end, use can be made, for example within the scope of image processing, of suitable filters and/or a trained machine learning method, for example a deep neural network trained for the identification of eyes, in particular a convolutional neural network. Training data comprising a multiplicity of annotated images of eye (areas) are used to train the machine learning method within the scope of a training phase.

An embodiment provides for the irradiance to be reduced in position-dependent fashion taking account of positions of the illuminated region which overlap with the eye area. As a result, it is possible in particular to take account of a specific hazard present for the eye area, which is to say a respective irradiance at the positions (in particular at the picture element coordinates). For example, using the specific value present at the considered position as a starting point, the irradiance might then only be reduced to such an extent that a hazard for the retina is no longer present there.

An embodiment provides for at least one (optical) marker arranged on a patient to be detected by means of a tracking system of the microsurgical visualization system and for a relative pose of the microsurgical visualization system vis-à-vis the at least one marker to be determined thereby, with the illuminated region being determined using the determined relative pose and properties of the at least one illumination source as a starting point. In particular, use can be made of a target with a plurality of (optical) markers. In particular, the relative pose contains information regarding a geometric relationship between the medical visualization system and the at least one marker. As a result, the illuminated region can be better determined since a geometric relationship between the microsurgical visualization system and the head of the patient is also known by way of the determined relative pose between the microsurgical visualization system and the at least one marker. As a result, it is possible to take account of the position of the head when determining the illuminated region. In particular, as a result, this allows an irradiance to be determined using a light field at the location of the head and/or of a face as a starting point, in particular by virtue of determining those positions of a surface of the head and/or face which coincide with the light field or at which the light field has a positive irradiance in the region of the head, more particularly of the face. In other words, the light field can be projected onto the head, in particular onto the face, for the purpose of determining the illuminated region (computationally or virtually), in order to determine the illuminated region on the basis of the projection.

An embodiment provides for a two-dimensional irradiance profile to be determined within the illuminated region, with the reduction being implemented taking account of position-dependent values of the irradiance profile. In particular, this allows position-dependent values of the irradiance within the overlap with the identified eye area to be taken into account during the reduction. In particular, this allows an irradiance to be reduced to such an extent in each case that the irradiance is below a dangerous value at the positions of the illuminated region which coincide with the identified eye area. For example, this value can be specified in the form of a limit value.

A refined embodiment provides for a relative depth profile of at least a part of the capture region to be determined for the purpose of determining the irradiance profile, using the captured image as a starting point, with the irradiance profile being determined using the determined relative depth profile and properties of the illumination source as a starting point. In particular, in that case, the irradiance profile is determined by virtue of the light field at the distance of a given mean working distance (e.g., at the location of the focal plane) being projected (computationally or virtually) onto the determined relative depth profile, in order to obtain a value for the irradiance for each two-dimensional position in this way. In particular, the relative depth profile is estimated with the aid of projective geometry. Using the captured image as a starting point, the relative depth profile can alternatively also be estimated by means of a machine learning method trained to this end. The trained machine learning method is trained to estimate a relative depth profile using captured images as a starting point. For example, a relative depth between the eyes and a tip of the nose or between other features of the face is estimated in the process. Within the scope of the training method for the machine learning method, pairs of images of faces and associated relative depth profiles, generated for example by measuring the faces imaged in the images, in particular, are used as training data. Further, the training data can additionally or alternatively also be generated by means of a simulation, in which images of faces are simulated on the basis of three-dimensional CAD data.

An embodiment provides for the at least one illumination source to be switched off or fully stopped down for reduction purposes. As a result, an illumination can be entirely suppressed. This embodiment can be implemented without much outlay. For example, it is possible to this end to interrupt a voltage supply of the at least one illumination source or move a stop into the beam path and/or into the light path by means of an actuator system configured for this purpose.

An embodiment provides for the at least one illumination source to be attenuated and/or masked in position-dependent fashion by means of an optical modulation device for the purpose of a reduction in the determined eye area. As a result, it is possible to reduce an irradiance only in the region of the identified eye area. Further, there can also be a position-dependent attenuation to an irradiance below a specified limit value. For example, a spatial light modulator (SLM) or a digital micromirror device (DMD), by means of which a light field can be modulated in two dimensions, can be used as optical modulation device.

An embodiment provides for the capture region to be at least partly captured by means of a stereoscopic camera system of the medical visualization system, and for a topography within the capture region to be determined using the captured stereoscopic images as a starting point, with the determined topography being taken into account when determining the illuminated region. As a result, it is possible to determine a topography of the head, more particularly of the face of the patient, and by using this as a starting point it is possible to project the light field from the at least one illumination source onto the surface of the face in order to determine the positions which are illuminated and consequently form the illuminated region. Further, this also allows improved determination of a position-resolved irradiance, by virtue of a respective irradiance being determined for the illuminated positions (by computational or virtual projection of the light field onto the surface).

Further features relating to the configuration of the microsurgical visualization system arise from the description of configurations of the method. The advantages of the microsurgical visualization system here are in each case the same as for the configurations of the method.

The invention is explained in greater detail below on the basis of preferred exemplary embodiments with reference to the figures. In the figures.

Figure 1:
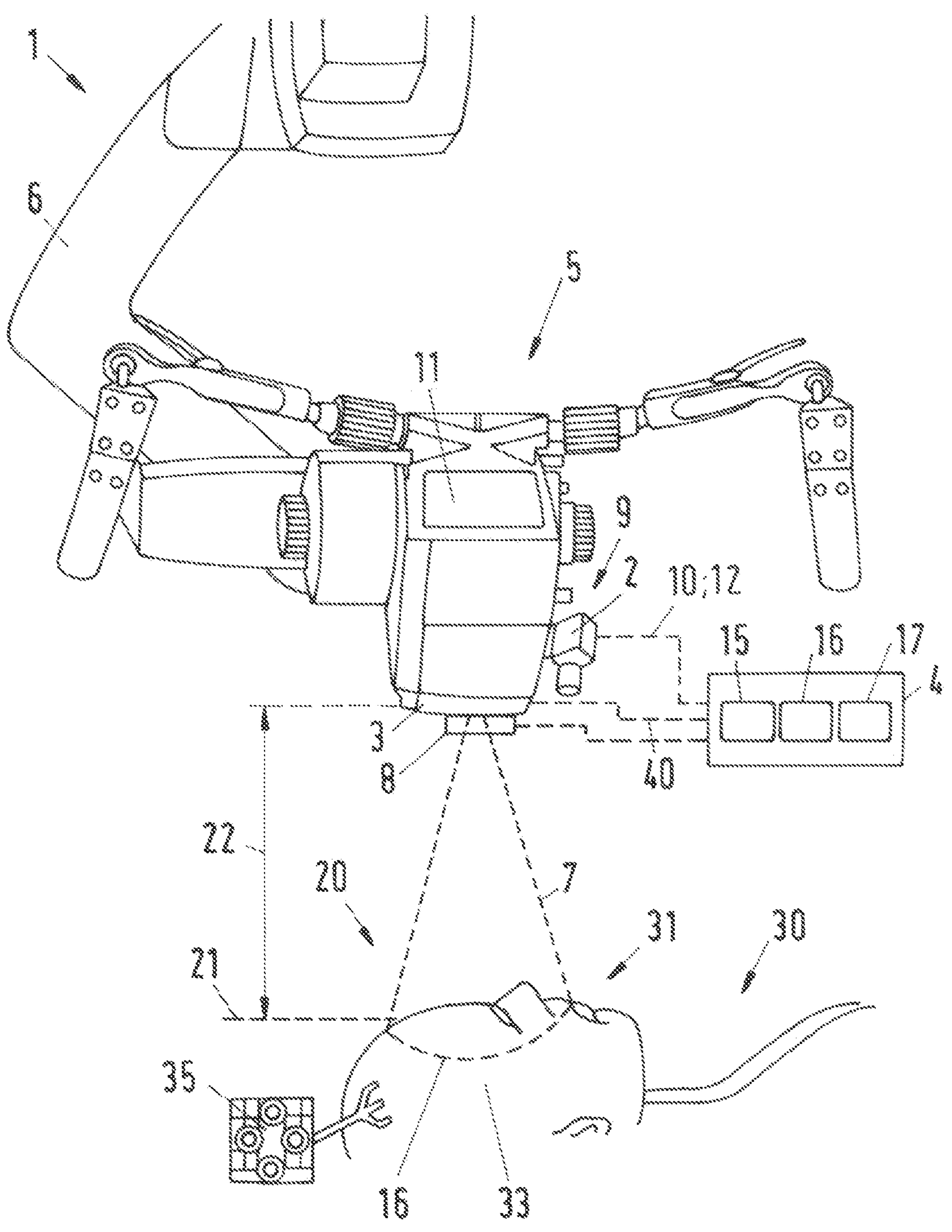
FIG. 1 shows a schematic illustration of an embodiment of the microsurgical visualization system.

FIG. 1 shows a schematic illustration of an embodiment of a microsurgical visualization system 1. In particular, the microsurgical visualization system 1 is a microsurgical surgical microscope. The microsurgical visualization system 1 is configured to perform the method described in this disclosure.

The microsurgical visualization system 1 comprises a camera 2, an illumination source 3, and a control device 4. For example, the camera 2 is a surround camera. However, the camera 2 can also be a camera which captures via an imaging optical unit (not shown) of a main observer beam path of the microsurgical visualization system. For example, the camera 2 and the illumination source 3 are arranged on a microscope head 5, which is arranged on a stand arm 6 and held by the latter.

The camera 2 is configured to capture a capture region 20. A head 33 of a patient 30 is arranged in the capture region 20. For example, a face 31 and/or a head 33 of the patient 30 is captured within the scope of a patient registration preceding a neurosurgical operation. For example, an area of the brain of the patient 30 is captured within a neurosurgical operation, which is to say in the case of an opened skullcap. In particular, provision is made for a target 35 with a plurality of optical markers to be arranged on the head 33 of the patient 30, and for this target to be intended to be captured and used within the scope of a patient registration.

The illumination source 3 is configured to illuminate at least a part of the capture region 20 and generates a light field 7 to this end.

The control device 4 is configured to identify a presence of an eye area 15 of the patient 30 in an image 10 captured by means of the camera 2. Further, the control device 4 is configured to identify a region 16 in the captured image 10 illuminated by the illumination source 3 and/or to determine the illuminated region 16.

Further, the control device 4 is configured to reduce an irradiance, at least in the identified eye area 15, by controlling the illumination source 3 if an overlap between the eye area 15 and the illuminated region 16 is ascertained.

Figure 2:
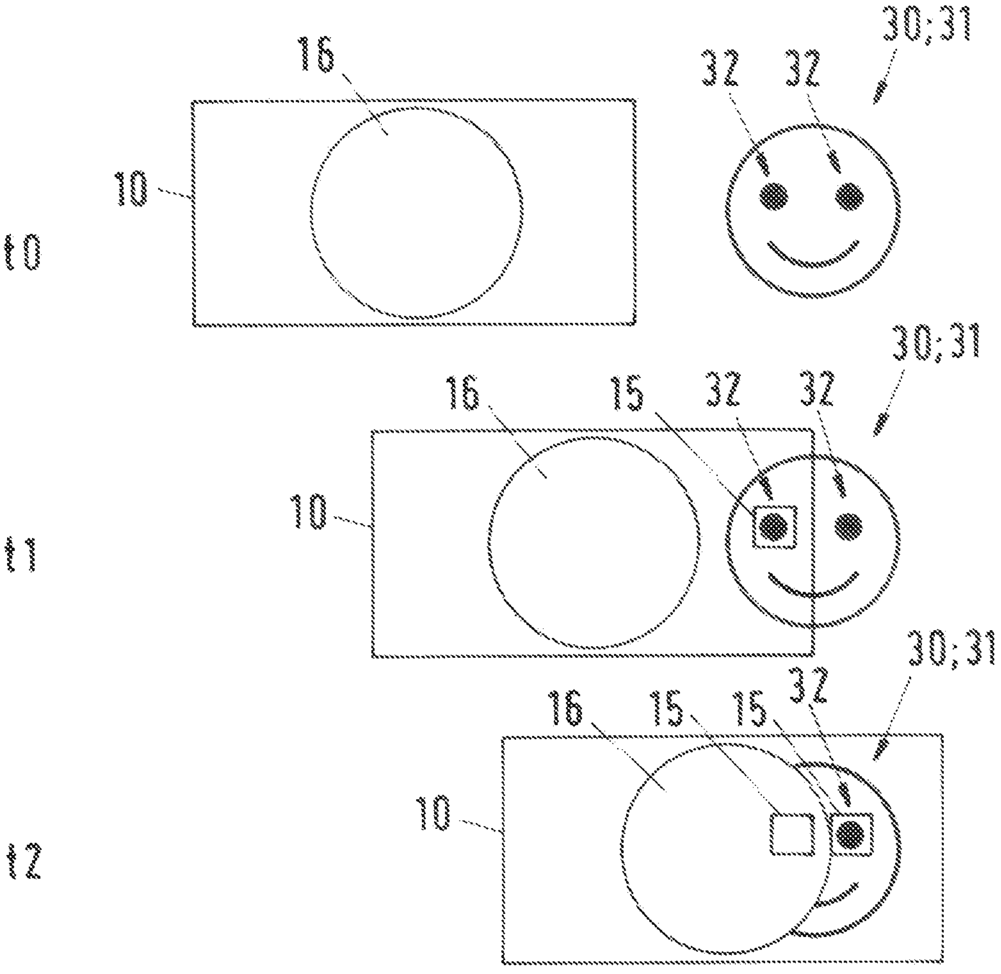
FIG. 2 shows a schematic illustration for elucidating the invention.

FIG. 2 shows a schematic illustration for elucidating the invention. A captured image 10 and the identified and/or determined illuminated region 16 in the captured image are depicted, in each case for three times t0, t1, and t2. The face 31 of a patient 30 with eyes 32 is also depicted. Since the camera and the illumination source are securely mechanically interconnected, at least in this example, the illuminated region 16 does not move relative to the image 10 if the camera and the illumination source are moved. At the time t0, there is no overlap between the illuminated region 16 and the eyes 32 of the patient. The camera and the illumination source are now moved in the direction of the patient (for example within the scope of a patient registration). At the time t1, the face 31 of the patient 30 is captured and an eye area 15 is identified for the left eye 32 (from the view of the surgeon or camera); however, there still is no overlap between the left eye 32 (and the identified eye area 15) and the illuminated region 16. However, the illuminated region 16 overlaps the left eye 32 and the identified eye area 15 at the time t2, and so an overlap is ascertained between the identified eye area 15 and the illuminated region 16. As a consequence, the irradiance of the illumination source is reduced.

Figure 3:
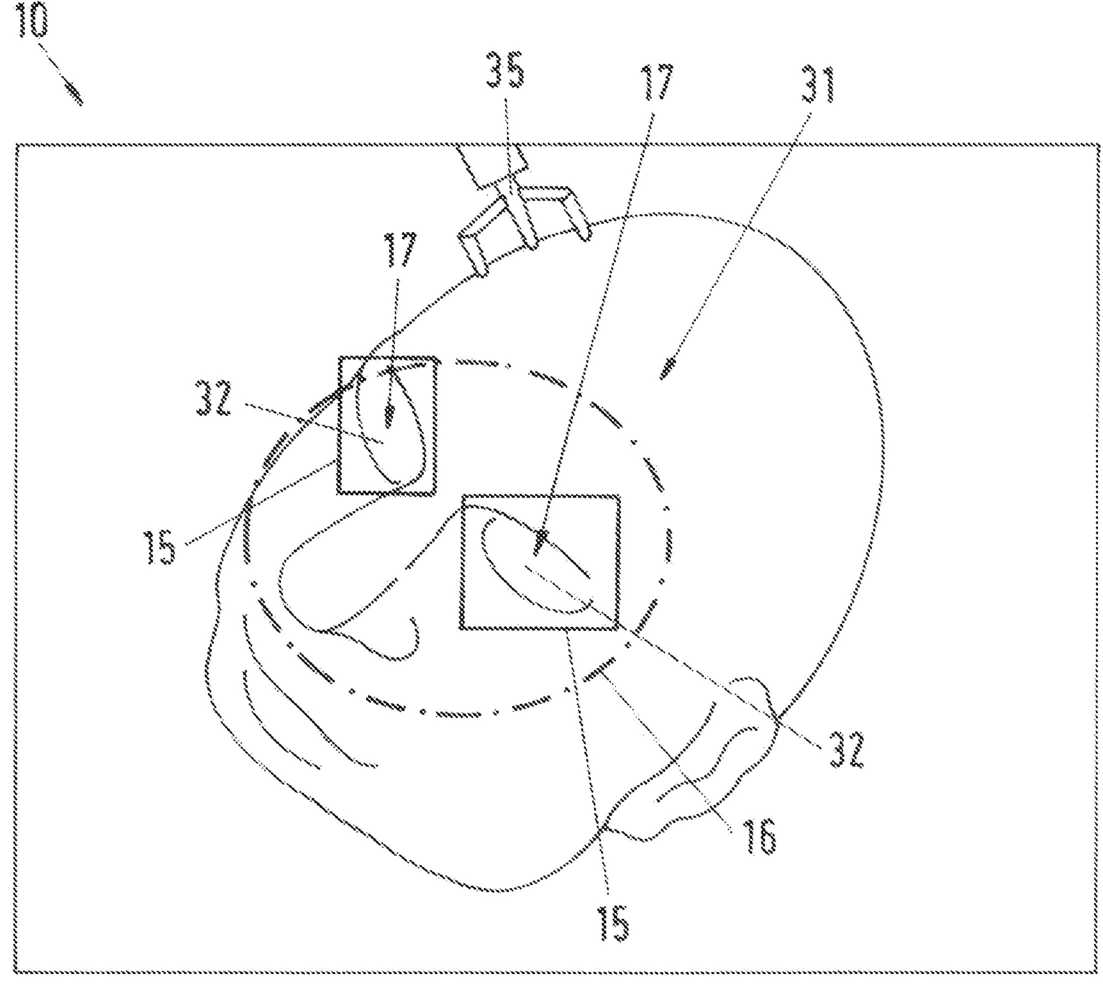
FIG. 3 shows a further schematic illustration for elucidating the invention.

Further, this is elucidated on the basis of FIG. 3, which schematically shows an image 10 captured by means of the camera 2. The image 10 contains an image of a face 31 (only indicated schematically here) of the patient 30. The identified eye area 15, which in each case comprises a portion for each one of the two eyes 32, is also depicted. In this case, the eye area 15 is marked by a bounding box in the example. For example, the eye area 15 can be identified by means of a trained machine learning method, for example by means of a convolutional neural network trained to this end.

Further, FIG. 3 shows the identified and/or determined illuminated region 16. For example, the illuminated region 16 is also identified by means of a (different) trained machine learning method, for example a convolutional neural network trained to this end. In particular, the illuminated region 16 is the region illuminated by the illumination source 3, which is to say the region of the face 31 in the shown example on which a light field 7 (FIG. 1) of the illumination source 3, propagating from an illumination origin, is incident. The intention is for the illuminated region 16 to be sharply delimited in the example shown and this is indicated by the ellipse; i.e., an irradiance jumps to zero upon departure from the illuminated region 16.

It is evident from FIG. 3 that there is an overlap between the eye area 15 and the illuminated region 16; i.e., in relation to the captured image 10, there is in particular a nonzero intersection between the eye area 15 and the illuminated region 16. In a simple example, as depicted here, the eye area 15 is formed as a rectangular picture region in the image 10. However, in principle the eye area 15 may also have a different shape, and for example correspond to an outer contour of the eyes 32.

The eye area 15 and the illuminated region 16 and the overlap are identified and/or determined and/or ascertained in particular with reference to positions or picture element coordinates in the captured image 10. In particular, the identified eye area 15 is defined using the picture element coordinates in the image 10 coinciding therewith as a starting point. Likewise, the illuminated region 16 is defined using the picture element coordinates in the image 10 coinciding therewith as a starting point. A comparison of the two sets of picture element coordinates can then be used to verify whether or not an overlap is present.

Since an overlap between the identified eye area 15 and the illuminated region 16 is ascertained in the example shown, an irradiance is reduced, at least in the identified eye area 15, by controlling the at least one illumination source 3. To this end, the control device 4 determines corresponding control signals 40 (FIG. 1) and transmits these to the illumination source 3.

By contrast, if it is ascertained that there is no overlap (anymore) at the current or a later time, then the irradiance is maintained or reset back to the original value.

In the simplest case, the irradiance is reduced by virtue of the illumination source 3 being switched off or completely stopped down for reduction purposes. Stopping down is implemented by means of a stop (not shown here) which is suitable to this end and in particular controlled accordingly by means of an actuator system (not shown here) configured to this end.

However, provision can also be made for the illumination source 3 to be attenuated and/or masked in position-dependent fashion by means of an optical modulation device 8 (FIG. 1) for the purpose of a reduction in the determined eye area 15. To this end and for the illumination source 3, the microsurgical visualization system 1 comprises such an optical modulation device 8, for example a spatial light modulator (SLM) or a digital micromirror device (DMD), which is controlled by means of the control device 4 and by means of which the light field 7 can be attenuated and/or masked in position-dependent fashion, which is to say in the region of the determined eye area 15 (FIG. 3).

Provision can be made for an eyelid status 17 to be identified in the captured image 10, the reduction in the irradiance being performed taking account of the identified eyelid status 17. In particular, the eyelid status 17 comprises at least the two states of "closed" and "open". However, in principle, it is also possible to identify and take account of intermediate states, in which for example the eye or the eyes 32 of the patient 30 are only partially open. The eyelid status 17 is identified by means of methods known per se, for example by means of a trained machine learning method, for example a trained neural network, in particular a trained convolutional neural network. Identification is performed by means of the control device 4. For example, by taking account of the identified eyelid status 17, the control device 4 is able to determine a value by which the irradiance must be reduced. Using the determined value as a starting point, the control device 4 determines control signals 40 and transmits these to the illumination source 3. As a rule, the irradiance can be reduced to a lesser extent for a closed eyelid status 17 than for an open eyelid status 17 in this case, since the retina is already protected by the closed eyelid.

Provision can be made for the irradiance to be reduced in position-dependent fashion taking account of positions of the illuminated region 16 which overlap with the eye area 15. In this case and using the known properties of the light field 7 as a starting point, provision can be made for an actual irradiance in the eye area 15 to be determined and/or estimated and for this determined and/or estimated irradiance to then be reduced to a target irradiance, independently of the size of the irradiance outside of the eye area 15. To this end, the control device 4 takes account of the irradiance within the picture elements in the captured image 10 which correspond to the eye area 15 in particular when reducing the irradiance.

Provision can be made for at least one target 35 with a plurality of markers arranged on a patient 30 to be detected by means of a tracking system 9 (FIG. 1) of the microsurgical visualization system 1 and for a relative pose of the microsurgical visualization system 1 vis-à-vis the markers of the target 35 to be determined thereby, with the illuminated region 16 being determined using the determined relative pose and properties of the at least one illumination source 3 as a starting point. On the basis of the identified markers of the target 35, it is possible in particular to determine and/or estimate a position and orientation of the face 31 of the patient 30, with the result that, using this and the known properties of the light field 7 of the illumination source 3 as a starting point, the illuminated region 16 (FIG. 1) can be determined, more particularly estimated, by virtue of the light field 7 being projected (computationally or virtually) onto a contour of the face 31.

In addition, a respective irradiance at various positions of the illuminated region 16 can also be determined thereby (in particular for various picture elements in the captured image 10). The respective values for the irradiance can then be taken into account in the reduction. Therefore, provision can be made for a two-dimensional irradiance profile to be determined within the illuminated region, with the reduction being implemented taking account of position-dependent values of the irradiance profile.

In a development, provision can be made for a relative depth profile of at least a part of the capture region 20 to be determined for the purpose of determining the irradiance profile, using the captured image 10 as a starting point, with the irradiance profile being determined using the determined relative depth profile and properties of the illumination source 3, in particular known properties of the light field 7 emanating from the illumination source 3, as a starting point. The irradiance profile is then determined by projecting the light field 7 on the determined relative depth profile, with the relative depth profile to this end being arranged (computationally or virtually) at a known working distance 22, for example in relation to a focal plane 21, relative to the microsurgical visualization system 1.

In particular, determining the relative depth profile comprises an estimate with the aid of projective geometry. In this case, relative distances between individual features of the face 31 are taken into account, for example an (average) distance between the tip of a nose and cheekbone, the eyes, etc. Further, machine learning methods trained to estimate relative depth profiles, for example a trained neural network, can also be used. Camera images, for each of which a relative depth profile was measured (this serves as ground truth), are supplied as input data to the neural network during a training phase. Using a camera image as a starting point, the neural network estimates a relative depth profile, and this is compared to the measured relative depth profile. The weights and/or parameters of the neural network are then adjusted during the training phase until a difference between the estimated and measured relative depth profile is below a given target value. The neural network trained thus is then used to estimate an associated relative depth profile in the method, using the captured image 10 as a starting point.

Provision can be made for the capture region 20 to be at least partly captured by means of a stereoscopic camera system 11 (FIG. 1) of the microsurgical visualization system 1, and for a topography within the capture region 20 to be determined using the captured stereoscopic images 12 as a starting point, with the determined topography being taken into account when determining the illuminated region 16. Then, in particular, the illuminated region 16 is determined by virtue of the known light field 7 of the illumination source 3 being projected onto the determined topography and the points (which coincide with picture elements in the image 10) at which the light field 7 strikes the topography in each case being assigned to the illuminated region 16. Moreover, a respective value for the irradiance can also be determined for these points by virtue of the respective value of the light field 7 at the point of incidence being calculated.

Figure 4:
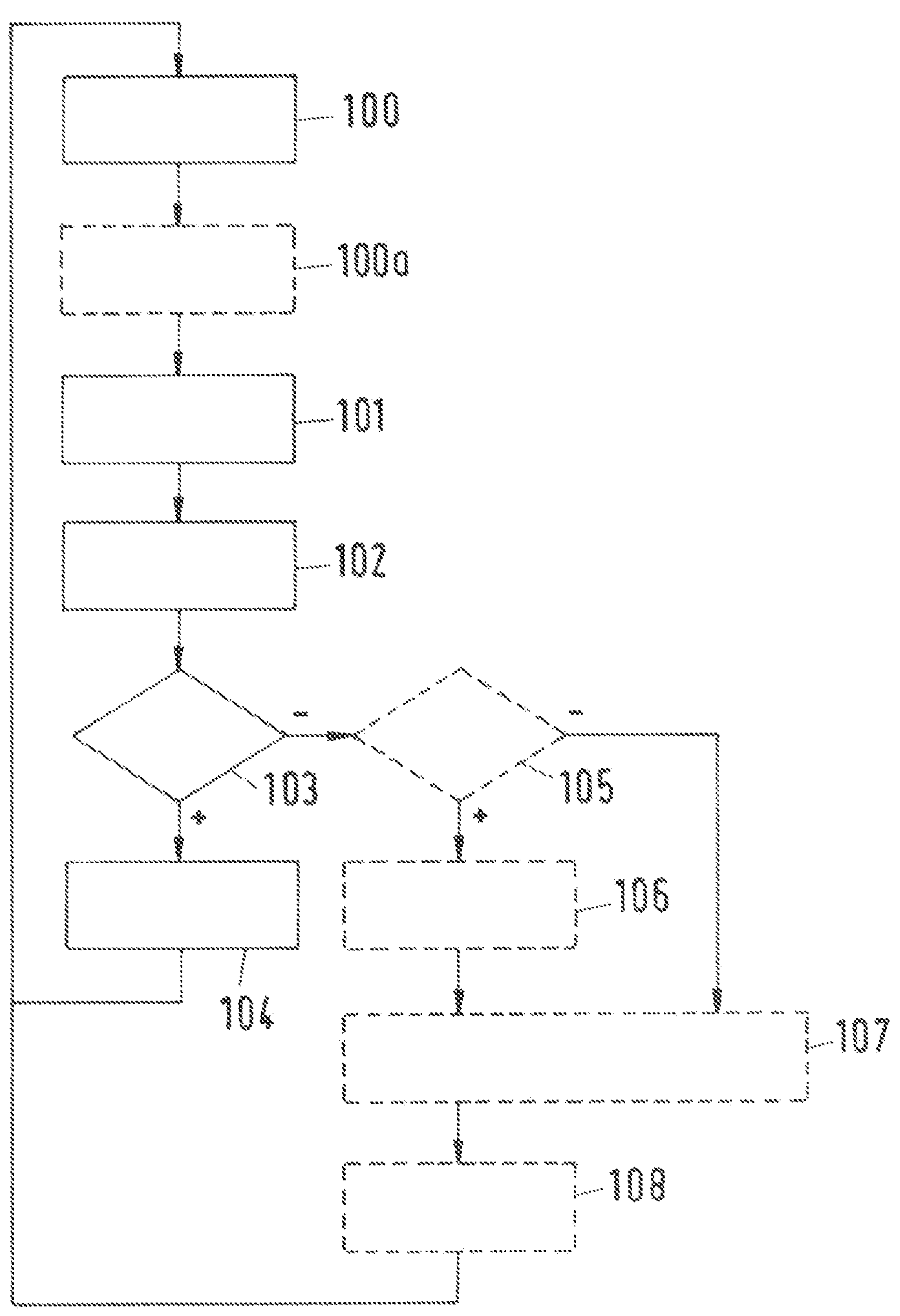
FIG. 4 shows a schematic flowchart of an embodiment of the method.

FIG. 4 shows a schematic flowchart of an embodiment of the method for operating a microsurgical visualization system. In particular, the microsurgical visualization system here is embodied in accordance with one of the above-described embodiments.

In particular, a target with a plurality of optical markers is arranged on a head of a patient captured by a tracking system when the method is applied. For example, the tracking system comprises a camera in the form of a surround camera, which is part of the microsurgical visualization system. An illumination source of the microsurgical visualization system illuminates at least a part of a capture region of a camera of the microsurgical visualization system. In particular, properties of the illumination source, in particular properties of a light field (geometry, spectrum, power, etc.) emanating from an illumination origin, are known in this case.

In a method step 100, the capture region is captured by means of at least one camera of the microsurgical visualization system and a captured image is provided. For example, the camera is the surround camera or a stereoscopic camera of the microsurgical visualization system.

A presence of an eye area of the patient in the captured image is identified in a method step 101. In this case, the eye area is defined as a picture element set within the captured image in particular.

In a method step 102, a region in the captured image illuminated by the at least one illumination source is identified and/or the illuminated region is determined. In this case, the illuminated region is defined in the form of a picture element set within the captured image in particular.

Whether an overlap is present between the eye area and the illuminated region is verified in a method step 103. By way of example, this is implemented by way of a comparison of the picture element sets, with an overlap being ascertained if the picture element sets have an intersection; that is to say if picture elements with identical picture coordinates are contained both in the picture element set of the eye area and in the picture element set of the illuminated region.

If an overlap is ascertained, an irradiance is reduced in a method step 104, at least in the identified eye area, by controlling the at least one illumination source. Examples of how the reduction can be performed have already been described above.

By contrast, if no overlap is ascertained, a renewed start can be made with method step 100, and so the method is repeated. In a method step 105, provision can be made for this to be preceded by verification as to whether or not there has already been a reduction in the irradiance. If such a reduction is present, the latter can be cancelled again in a method step 106. Otherwise, it is possible to directly continue with method step 100.

In a method step 100*a*, provision can be made for at least one marker arranged on a patient to be detected by means of an (internal) tracking system of the microsurgical visualization system and for a relative pose of the microsurgical visualization system vis-à-vis the at least one marker to be determined thereby, with the illuminated region being determined in method step 102 using the determined relative pose and properties of the at least one illumination source as a starting point.

Provision can be made for method steps 100 to 106 to be used within the scope of a stereoscopic capture and a determination of a topography within the capture region.

In particular, provision is then made for the capture region to be at least partly captured by means of a stereoscopic camera system of the microsurgical visualization system in a method step 107, and for a topography within the capture region to be determined using the captured stereoscopic images as a starting point in a method step 108, with the determined topography being taken into account when determining the illuminated region in method step 102.

Method steps 100*a*, 101, and 102 can also be carried out simultaneously.

Further embodiments of the method were already described hereinabove with reference to the microsurgical visualization system.

LIST OF REFERENCE SIGNS

1 Microsurgical visualization system
2 Camera
3 Illumination source
4 Control device
5 Microscope head
6 Stand arm
7 Light field
8 Optical modulation device
9 Tracking system
10 Captured image
11 Stereoscopic camera system
12 Stereoscopic image(s)
15 Identified eye area
16 Illuminated region
17 Eyelid status
20 Capture region
21 Focal plane
22 Working distance
30 Patient
31 Face
32 Eye
33 Head
35 Target with a plurality of (optical) markers
40 Control signal
100-108 Method steps

The invention claimed is:

1. A method for operating a microsurgical visualization system, wherein the microsurgical visualization system comprises at least one camera for capturing a capture region and at least one illumination source for illuminating at least a part of the capture region, wherein a presence of an eye area of a patient in an image captured by means of the at least one camera is identified, wherein a region in the captured image illuminated by the at least one illumination source is identified and/or the illuminated region is determined, and wherein an irradiance is reduced, at least in the identified eye area, by controlling the at least one illumination source if an overlap between the eye area and the illuminated region is ascertained.

2. The method as claimed in claim 1, wherein an eyelid status is identified in the captured image, the reduction in the irradiance being performed taking account of the identified eyelid status.

3. The method as claimed in claim 1, wherein the irradiance is reduced in position-dependent fashion taking account of positions of the illuminated region which overlap with the eye area.

4. The method as claimed in claim 1, wherein at least one marker arranged on a patient is detected by means of a tracking system of the microsurgical visualization system and a relative pose of the microsurgical visualization system relative to the at least one marker is determined thereby, with the illuminated region being determined using the determined relative pose and properties of the at least one illumination source as a starting point.

5. The method as claimed in claim 1, wherein a two-dimensional irradiance profile is determined within the illuminated region, with the reduction being implemented taking account of position-dependent values of the irradiance profile.

6. The method as claimed in claim 5, wherein a relative depth profile of at least a part of the capture region is determined for the purpose of determining the irradiance profile, using the captured image as a starting point, with the irradiance profile being determined using the determined relative depth profile and properties of the illumination source as a starting point.

7. The method as claimed in claim 1, wherein the at least one illumination source is switched off or fully stopped down for reduction purposes.

8. The method as claimed in claim 1, wherein the at least one illumination source is attenuated and/or masked in position-dependent fashion by means of an optical modulation device for the purpose of a reduction in the determined eye area.

9. The method as claimed in claim 1, wherein the capture region is at least partly captured by means of a stereoscopic camera system of the microsurgical visualization system, and a topography within the capture region is determined using the captured stereoscopic images as a starting point, with the determined topography being taken into account when determining the illuminated region.

10. A microsurgical visualization system, comprising:

at least one camera configured to capture a capture region, at least one illumination source configured to illuminate at least a part of the capture region, and a control device, wherein the control device is configured to identify a presence of an eye area of a patient in an image captured by means of the at least one camera, to identify a region in the captured image illuminated by the at least one illumination source, and/or to determine the illuminated region, and to reduce an irradiance, at least in the identified eye area, by controlling the at least one illumination source if an overlap between the eye area and the illuminated region is ascertained.

11. The method as claimed in claim 9, wherein the stereoscopic camera system further comprises a plurality of cameras, the plurality of cameras including a stereo camera.

12. The method as claimed in claim 11, wherein the plurality of cameras includes a surround camera configured to capture a surround of the capture region, and the surround camera being a stereo camera that is integrated into the stereoscopic camera system.

* * * * *